US005486304A

United States Patent [19]
Eoga et al.

[11] Patent Number: 5,486,304
[45] Date of Patent: Jan. 23, 1996

[54] FRAGRANT DENTURE CLEANSER COMPOSITION

[75] Inventors: Anthony B. Eoga, Boonton; Richard G. Moran, Lake Hopatcong, both of N.J.

[73] Assignee: Warner-Lambert Company, Morris Plains, N.J.

[21] Appl. No.: 322,889

[22] Filed: Oct. 13, 1994

Related U.S. Application Data

[63] Continuation of Ser. No. 160,378, Dec. 1, 1993, Pat. No. 5,384,062.

[51] Int. Cl.$^6$ .............................. A61K 7/30; C11D 3/39; C11D 3/48; C11D 17/00
[52] U.S. Cl. ............................ 252/99; 252/95; 252/102; 252/106; 252/174; 252/174.12; 252/174.23; 252/527; 252/DIG. 2; 252/DIG. 11; 252/DIG. 12; 252/DIG. 16
[58] Field of Search ................................ 252/95, 99, 102, 252/106, 174, 174.12, 174.23, 527, DIG. 2, DIG. 11, DIG. 12, DIG. 16

[56] References Cited

U.S. PATENT DOCUMENTS

| 4,155,868 | 5/1979 | Kaplan et al. | 252/95 |
| 5,384,062 | 1/1995 | Eoga et al. | 252/99 |

FOREIGN PATENT DOCUMENTS

| 253772 | 1/1988 | European Pat. Off. |
| 9210165 | 6/1992 | WIPO |

*Primary Examiner*—Paul Lieberman
*Assistant Examiner*—Alexander G. Ghyka
*Attorney, Agent, or Firm*—Michael J. Atkins

[57] ABSTRACT

An anhydrous denture cleansing composition is disclosed comprising anhydrous perborate, a perborate monohydrate, a lubricant and compression aid, a monopersulfate, a sequestering agent, and, optionally, excipients, builders, colors, flavors, and surfactants.

41 Claims, No Drawings

FRAGRANT DENTURE CLEANSER COMPOSITION

CROSS-REFERENCE TO RELATED APPLICATIONS

This is a continuation of application Ser. No. 08/160,378 filed on Dec. 1, 1993, now U.S. Pat. No. 5,348,062.

BACKGROUND OF THE INVENTION

1. Field of the Invention

The invention relates to a denture cleansing composition which does not contain enzymes and can effectively remove stains similar to known denture cleansing formulations, and a process for making such a composition. The composition also exhibits longer lasting fragrance retention over known denture cleansing formulations. This is especially true for those who soak their dentures overnight.

2. Description of the Related Art

Denture cleansing generally is carried out either by brushing dentures with a paste or by soaking dentures overnight in an aqueous cleansing solution. Aqueous denture cleanser solutions are known and generally compose tablets, granules, or powders that are dissolved in water to form a cleansing bath or cleansing system in water.

Denture cleansing compositions, such as effervescent tablets and powders, are well known in the art. Traditionally, these compositions have contained a variety of sulfate salts, such as bisulfates, monopersuifates, and sulfates as detergents, oxidizers and the like, and have also utilized alkali metal and alkaline earth metal halides as bleaches. Such compositions have also included perborate, carbonate and phosphate salts in varying amounts to provide effervescence and activation. Representative examples of cleansing compositions covering these various materials are set forth in U.S. Pat. Nos. 3,337,466, 3,704,227, 4,362,639 and 4,857,224.

The cleansing systems produced by these compositions when dissolved in water have drawbacks. The pH of the aqueous solution is too low (i.e. too acidic) for the retention of fragrances. In addition, the reaction of monopersulfates in the compositions with chlorides in the water produces a hypochlorite which reacts with expensive fragrances in the compositions, depressing their efficacy. Moreover, known denture cleansers can be formulated to provide an initial fragrance level when the cleanser is in a tablet form, but they cannot be formulated to maintain the level of fragrance upon dissolution without compromising the hardness of the tablet, or maintain the level of fragrance when the resultant solution is allowed to stand overnight.

The fragrance of a denture cleaning composition in aqueous solution is an important feature. The sweet or pleasant odors which emanate from the compositions are due to the introduction of ingredients such as oils. The presence of a fragrance is aesthetically pleasing to a consumer, as well as an indicator to a consumer that a product works effectively. Consumers are more likely to purchase a denture cleanser characterized as having longer fragrance retention levels. This is especially true for those who soak their dentures overnight.

In addition, many denture cleansing compositions feature the use of alkaline proteolytic enzymatic cleansing agents. The use of enzymes in denture cleansing compositions, however, has many drawbacks. The pH of the aqueous solutions of many systems is too low for fully effective cleaning enzyme activity. Also, the reaction of the monopersulfate in the compositions with chlorides in the water produces hypochlorite which inactivates the cleaning enzymes in the compositions, further depressing their efficacy.

Moreover, the use of enzymes is expensive. The high cost of using enzymes is due not only because the enzymes themselves are expensive, but also because manufacturing facilities must be especially designed to safely incorporate and handle enzymes. This is particularly true in the United States where stringent governmental regulations require special equipment and operating procedures which increases not only the ultimate cost of manufacturing denture cleansing compositions, but also increases the time which is required to produce these compositions.

There have been efforts, with limited success, to develop a denture cleansing compositions that do not comprise the use of enzymes and in which fragrance instability does not occur, while still providing good denture cleaning efficacy.

U.S. Pat. No. 4,409,118 to Anthony Eoga, issued Oct. 11, 1983, discloses an effervescent cleansing composition in tablet form comprising: (1) a phosphate salt; (2) a silicate salt; and (3) at least one perborate salt. At least part of the perborate salt is in a compacted granulated mixture with a polymeric fluorocarbon.

U.S. Pat. No. 4,857,224, to Anthony Eoga, issued Aug. 15, 1989, discloses an effervescent cleansing composition in tablet form comprising: (1) a pregranulated and compressed mixture of an anhydrous perborate, a perborate monohydrate and a polymeric fluorocarbon compound, and (2) a monopersulfate compound. This composition is useful for forming a tablet from monopersulfates and anhydrous perborates.

SUMMARY OF THE INVENTION

One object of the invention is to provide a denture cleansing composition with reduced hypochlorite formation, thereby eliminating the problem of fragrance instability.

A further object of the invention is to provide a denture cleansing composition capable of dissolving in an aliquot of water to produce a denture cleansing bath having a pH which does not lead to fragrance instability.

A further object of the invention is to provide a denture cleansing composition which does not require the presence of cleaning enzymes thereby representing a significant savings in cost, A further object of the invention is to provide a denture cleansing composition that provides an initial fragrance and provides a burst of fragrance upon dissolution of the composition in water, and retains a substantial amount of fragrance when the resultant solution is allowed to stand overnight.

A further object of the invention is to provide a denture cleansing composition capable of removing non-stained plaque, stained plaque, non-stained tartar, stained tartar, and any residue or aftertaste which appears to result from a combination of plaque, stained plaque, tartar and stained tartar.

A further object of the invention is to provide a superior denture cleansing composition that does not require added water in the composition or curing of the composition in tablet form.

A further object of the invention is to provide a denture cleansing composition in tablet form with fragrances that is compressible at the high speeds necessary for commercial production, yet retains its efficacy and stability.

A further object of the invention is to provide a denture cleansing composition in tablet form capable of being compressed to a hardness of at least about 15 SCU.

Additional objects and advantages of the invention will be set forth in part in the description that follows. The objects and advantages of the invention may be realized and attained by means of the examples and combinations described in detail herein and in the appended claims.

These and other objectives are achieved by the present invention, which relates to new denture cleansing compositions and their method of preparation comprising:

(a) a pregranulated compressed mixture of an anhydrous perborate, a perborate monohydrate and a lubricant and compression aid;

(b) a monopersulfate compound;

(c) non-granulated perborate monohydrate;

(d) an effective amount of sequestering agent such as ethylene diamine tetracetic acid (herein "EDTA") to remove calcium deposits and calculus (also referred to herein as "tartar" deposits); and (e) an effervescence-producing composition, wherein the ratio of anhydrous perborate and monohydrate perborate to monopersulfates and the sequestering of calcium and calculus deposits results in the removal of calculus and plaque deposits and stains as well as the retention of fragrances.

DETAILED DESCRIPTION OF THE INVENTION

The present invention relates to improved denture cleansing compositions containing EDTA, a monoporsulfate, anhydrous perborate, perborate monohydrate, and polymeric fluorocarbon that has excellent cleaning properties and that can be easily tableted and packaged using high speed equipment. The invention also provides a denture cleansing composition that exhibits a pronounced fragrance, that provides a burst of fragrance when dissolved in solution, and that provides for an enhanced fragrance retention in solution overnight. The invention also provides a denture cleansing composition for efficient cleaning of the dentures by brushing. The invention further provides for the removal of residue from dentures after simple rinsing of the dentures under warm water.

The inventive composition is unique in solving some of the fragrance and cleaning problems associated with the inclusion of persulfate compounds in denture cleansing tablets. The new inventive composition provides cleaning efficacy and fast dissolution as required of denture cleansers. In addition, the ratio of the components of this denture cleanser react less with the fragrance additives than the ratio of the components of other denture cleansers. Therefore, less fragrance additives are needed to produce the desired fragrance effect, thereby lowering the cost. Additionally, the tablets or granulations formed from these new compositions exhibit a strong fragrance. The solution formed from the tablets or granulations provides an initial burst of fragrance, and the solution retains a substantial amount of fragrance when used for soaking dentures overnight.

The capability of a aqueous solution of a denture cleansing composition to retain fragrances is dependent primarily upon active oxygen levels, the type of active ingredients and the pH of the final solution. An active oxygen level is defined as the percent of reactive oxygen which is released in solution from oxygen precursors known to those of skill in the art, such as perborates, persulfates or peroxides. Fragrance retention is defined as the ability of the fragrance to retain a substantial amount of the fragrance profile over a period of time. Effervescent formulations in the form of powders or tablets containing oxygen precursors dissolve and release an effervescent gas such as oxygen. The gas bubbles, as they pass the denture, contribute a gentle mechanical cleansing action and thus help to remove particulate matter and tend to remove stains thereon and provide antiseptic action. In addition, the oxygen acts as a vehicle for fragrances to be released to the surrounding environment providing a aesthetically pleasing aroma.

Traditionally, the leading known commercial denture cleansing compositions contain active oxygen levels in the range from about 60 to about 115 mg/tablet. The active oxygen levels remaining in a denture cleansing solution after a period of about six hours is in the range from about 20% to about 25%.

The denture cleansing compositions of the present invention, however, contain active oxygen levels in the range from about 100 to about 200 mg/tablet, preferably in the range from about 120 to about 170 rag/tablet, most preferably in the range from about 130 to about 165 mg/tablet. The active oxygen levels remaining in a denture cleansing solution after a period of six hours or greater is about 50%, preferably in the range from about 60% to about 90%, most preferably in the range from about 80% to about 90%. Moreover, the denture cleansing compositions of the present invention while in solution have active oxygen levels remaining after a period of 16 hours or greater than 50%, preferably in the range from about 60% to about 90%, most preferably in the range from about 80% to about 90%.

Without intending to be bound by theory, the compositions of the present invention uses an excess of perborate monohydrate over any persulfates. The reaction essentially completely depletes the persulfates while reserving sufficient amounts of oxygen precursors to provide high active oxygen levels, thus preventing the formation of hypochlorites due to the chlorides in the raw materials and aqueous solution. As discussed above, hypochlorites are known to destroy fragrances which are present in the product for cleaning and consumer acceptance. Thus, the fragrance becomes readily available not only as a burst of fragrance when the composition is dissolved in water, but it also provides retained fragrance over an extended period of time.

The anhydrous perborate is preferably an alkali metal perborate or an alkaline earth metal perborate. The amount of anhydrous perborate in the composition can be between about 5% and about 25% by weight of the composition, preferably the amount of anhydrous perborate in the composition is between about 10% and about 20% by weight of the composition, most preferably the amount of anhydrous perborate in the composition is between about 13% and about 14% by weight of the composition. The amount of perborate monohydrate in the composition can be between about 30% to about 60% by weight of the composition, preferably the amount of perborate monohydrate in the composition is between about 30% and about 40% by weight of the composition, most preferably the amount of perborate monohydrate in the composition is between about 33% and about 35% by weight of the composition.

The weight ratio of anhydrous perborate to perborate monohydrate in the composition is from about 1:3 to about 1:1. The preferred perborate monohydrate is a non-compacted sodium perborate monohydrate in the form of a predried product containing about 0.3% to about 1.5% by weight of water, and preferably less than about 0.2% to about 0.3% by weight of water.

The invention also comprises lubricant and compression aids. Lubricant and compression aids insure good release of the tablet from the tablet die and are well known in the art. Sodium lauryl sulfate, sodium benzoate, polyethylene glycol, talc, metal stearates and polymeric fluorocarbons are all known and acceptable lubricants and compression aids. Although it is insoluble, polytetrafluoroethylene (herein "PTFE") is the preferred lubricant and compression aids. The lubricant and compression aid comprises from about 0.1% to about 0.8% by weight of the pregranulation mixture of anhydrous perborate, sodium perborate monohydrate, and polymeric fluorocarbon.

Where a high degree of initial solution clarity is needed, the PTFE may be present in the amounts from about 0.1% to about 0.8%, and more preferably from about 0.5% to about 0.7% PTFE by weight of the composition. Although PTFE is insoluble, its use within the limit ranges described herewith results in the majority of the PTFE becoming entrapped in the effervescent foam and the solution appears relatively clear.

The monopersulfate compound used in the composition is preferably an alkali metal monopersulfate or an alkaline earth metal monopersulfate. A preferred salt is potassium monopersulfate, especially when present in the form of a triple salt compound with potassium bisulfate and potassium sulfate, e.g. $KHSO_5 \cdot K_2SO_4 \cdot K_2SO_4$. This stable triple potassium salt is available commercially from E. I. duPont DeNemours & Co., Inc. and is sold in the mole ratio 2:1:1 under the trademark "OXONE."

The "OXONE" used in the composition is from about 15% to about 27% by weight of the total composition, preferably from about 18% to about 23%, and most preferably from about 20% to about 21%.

Sequestering agents are added to the tablet to maintain clarity and to promote calculus, or tartar, removal. The sequestering agent also helps to stabilize any hydrogen peroxide present. Hydrogen peroxide is generated from sodium perborate monohydrate which reacts with heavy metals to form $H_2O + +O_2$, thereby reducing the active oxygen content. The EDTA chelates any metals in the solution before they can react with the hydrogen peroxide.

Preferred sequestering agents include ethylene diamine tetraacetic acid ("EDTA") and its corresponding alkali salts, as well as other polyfunctional organic acids, such as citric acid, maleic acid, fumaric acid, phosphates, phosphonates, pyrophosphates, and their corresponding salts. The EDTA may be present in amounts of about 1% to 25% by weight of the composition, preferably about 17% to about 23% by weight of the composition, and most preferably about 19% to 21% by weight of the composition.

The EDTA is preferably present as $Na_4EDTA \cdot 2H_2O$, and is preferably dried to a chelating value of 248 or more such that the chelating value is at a sufficient level to compensate for the water which is present in the composition.

In one preferred embodiment of the present invention, the EDTA is milled to a U.S.S. mesh size profile in the range of a maximum of 40% through U.S.S. 100 mesh sieve, a maximum of 65% on the U.S.S. 40 mesh sieve and a maximum of 0.2% remaining on the U.S.S. 20 mesh sieve. In another preferred embodiment of the present invention, the EDTA is milled to a U.S.S. mesh size profile in the range of a maximum of 20% through U.S.S. 100 mesh sieve, a maximum of 65% on the U.S.S. 40 mesh sieve and a maximum of 0.2% remaining on the U.S.S. 20 mesh sieve. Most preferably, EDTA is milled to a U.S.S mesh size profile of:

Maximum of 0.2% on U.S.S. 20 Mesh
Maximum of 25% on U.S.S. 40 Mesh
Maximum of 20% through U.S.S. 100 Mesh The use of EDTA with a mesh-size profile of greater than 25% through U.S.S. 100 mesh results in the preparation of a table with reduced hardness.

Without intending to be bound by theory, it is believed that the sequestering agent functions in the solution of the invention by reacting with the calcium present in the calculus that accumulates on dentures during the day. This reaction renders underlying proteinaceous material, i.e., plaque, on the dentures susceptible to attack by a persulfate compound also present in the solution. The persulfate compound in turn attacks this plaque, thereby exposing more calculus to attack by the sequestering agent. Any stain attached to the above deposits are also removed in the process.

This synergistic combination of persulfate compound and sequestering agent in a denture cleansing composition allows for a more complete removal of both plaque and calculus on dentures. Adsorbed stains, especially those due to accumulated calculus, that had been beyond the reach of single cleansing ingredients are also susceptible to removal by the tablet of this invention.

Free halogens, especially chlorine, typically found in tap water and other raw materials, can inactivate fragrances in a system that also includes perborate and monopersulfate. Fragrances are destroyed by hypochlorites which are formed by the association of persulfates and chlorides in the raw materials. This invention overcomes this problem by using a weight ratio of from about 3:1 to about 1:1, more preferably about 1.7:1, of perborate monohydrate to "OXONE". This ratio reduces the formation of hypochlorite and free chlorine. In a system with this perborate/persulfate ratio range, fragrances are not inactivated and are more available as a burst of fragrance when a tablet is dissolved in water. It also provides for retained fragrance overnight.

Colorants and fragrances may also be used with the composition of this invention. F.D.& C. and D.& C. dyes and lakes and natural colors may be used. The materials acceptable for the foregoing spectrum of use are preferably water soluble, but they may include water insoluble dye materials found in the Kirk-Othmer Encyclopedia of Chemical Technology, Volume #5, pages 857–884, which text is hereby incorporated herein by reference.

The fragrance is preferably spray added and prepared to a free moisture content of less than about 5.0% and preferably less than about 3.0%.

The fragrances can be any known free flavor or fragrance oil. For example, one fragrance can be selected from the group consisting of thymol, eucalyptol, methyl salicylate, menthol, peppermint oil and spearmint oil.

One preferred embodiment of the invention is a water soluble effervescent denture cleanser composition, which comprises the novel steps of: (a) preparing an anhydrous perborate, perborate monohydrate and polymeric fluorocarbon compound as a first premix; (b) forming a precompressed pregranulation or plurality of particles therefrom such that the particles are of a size which will promote cohesion of the final tablet; and (c) combining this premix with the other components as described in Examples 1–2, hereinbelow.

In this preferred embodiment of the inventory, the other components of the composition in tablet form are dried to a free surface moisture content of from about 0.02% to about 2% by weight of the composition.

Tablets made from the composition of the invention exhibit excellent hardness, on the average of at least about 12 SCU, preferably from about 18 SCU to about 20 SCU. The tablets have demonstrated even higher hardness levels, which allows the manufacturer to choose an appropriate hardness level that will permit disintegration in water at an appropriate rate and consequently an appropriate fade time.

The materials must be in the proper range of mesh size, otherwise tablets produced from the materials may be defective, and exhibit "capping" during the compression stage. In addition, if particles are too large the tablets may not dissolve fast enough. The particle size especially affects the dissolution of EDTA. Particle size also affects the hardness of the tablet.

When added to water the tablets produce a blue colored cleansing bath. This blue color fades after about 3–10 minutes. The rate of fading depends upon the ratio of the persulfate to the perborate, the water bath temperature, and the amount of water used for the bath and the rate of disintegration.

Tablets dissolved in water form a cleansing solution that removes plaque, stain and tartar deposits from dentures. The amount of plaque, stain, and tarter deposits removed is also dependant upon the amount of time the denture is soaked in the cleansing solution. Rinsing the dentures after soaking will aid in removing the residual denture cleanser solution and additional plaque, stain, and tartar. It is believed that rinsing may also reduce the "slippery" or "slimy" feeling or the "metallic aftertaste" often associated with dentures immediately following the cleaning process with commercial denture cleansers.

It should be understood that although the present invention is particularly useful for forming a tablet, it is not limited in this regard. The present invention generally discloses a denture cleansing composition which is comprised of certain specified ingredients. This denture cleansing composition will in one embodiment be used to form a tablet, yet in another embodiment, the composition will be used in a different pharmaceutical delivery system, such as a granulation or dispersible powder.

A further understanding of the present invention will be gained from the following illustrative examples.

Example 1–3

Methods of preparation:

The compositions set forth in Examples 1–3 were prepared as follows. The amounts of each ingredient in the composition are set forth in Table 1.

Example 1 was prepared as follows: A pregranulation mix, or premix, was prepared containing anhydrous sodium perborate, sodium perborate monohydrate, and a small amount of PTFE. The three premix ingredients were combined in a ratio of 14.7/23.9/0.15. All of the anhydrous perborate was used in the premix. The amounts of perborate monohydrate and PTFE in the premix reflect the aforesaid ratio. These three components were blended in a Day blender for about 3 minutes and passed through a chilsonating compacting machine, Model DMC Fitzpatrick, under the following conditions: The chilsonator was set at an air pressure of from about 88 to about 90 psi, and oil pressure of from about 2300 to about 2400 psi, and the roller at high speed using 2–3 amps. The compacted material was then passed through a Model 197S comil having an 0.175 inch spacer, with an 0.032 inch screen at 4200 RPM. The compacted anhydrous perborate, perborate monohydrate and PTFE, hereinafter known as the premix, typically had a U.S.S. Mesh distribution of:

14% on a size 40 mesh screen,
22% on a size 60 mesh screen,
15% on a size 80 mesh screen,
16% on a size 100 mesh screen,
33% through a 100 mesh screen.

The premix had an untapped density of 0.58 grams/ml and a tapped density (100 taps) of 0.79 grams/ml.

The premix as prepared is used in the formulation at approximately 7% by weight.

In a suitable blender container set at 50 RPM the following ingredients were combined in sequence in evenly spaced intervals: sodium bicarbonate; dyes and water; sodium tripolyphosphate; sodium carbonate; citric acid; EDTA; "OXONE"; the remainder of the unpregranulated sodium perborate monohydrate; the premix; flavor preblend; sodium saccharin; spray dried fragrance; sodium sulfate; "LATHANOL"; sodium benzoate. The remainder of the PTFE was then added and mixed for an additional 3 minutes. The resultant mixture was compressed into a tablet having a diameter of from 27/32" to 15/16", a thickness of approximately 0.190" to 0.151", and a minimum hardness of 12 SCU.

For examples 2–3, a premix was prepared containing anhydrous sodium perborate, sodium perborate monohydrate, and PTFE in the ratio of 45.26/54.18/0.56. All of the anhydrous perborate was used in the premix. The amounts of perborate monohydrate and PTFE in the premix reflect the aforesaid ratio. These three components were blended in a blender for about 3 minutes and passed through a chilsonating compacting machine, Model DMC Fitzpatrick, under the following conditions: The chilsonator was set at an air pressure of 89 psi, the oil pressure was set at 2350 psi and the roller at high speed using 2–3 amps. The compacted material was then passed through a Model 1972 comil having 0.175 inch spacer, with an 0.032 inch screen at 4200 RPM. The compacted anhydrous perborate, perborate monohydrate and PTFE, hereinafter known as the premix, typically had a U. S.S. Mesh size distribution of:

14% on a size 40 mesh screen,
25% on a size 60 mesh screen,
11% on a size 80 mesh screen,
15% on a size 100 mesh screen,
35% through a 100 mesh screen.

The premix had an untapped density of 0.58 grams/ml and a tapped density (100 taps) of 0.76 grams/mi.

For best results, the moisture content of the sodium perborate monohydrate should be less than 0.6%. The premix as prepared is used in the formulation at approximately 25% by weight.

After the premix was prepared, the preparation of Examples 2–3 was completed as follows: In a suitable blender set at 50 RPM the following ingredients were added in sequence at approximately 90-second intervals; the remainder of the non-pregranulated sodium perborate monohydrate that was not used to prepare the premix; EDTA; potassium monopersulfate; the premix; sodium tripolyphosphate; a preblend of the dyes and sodium bicarbonate and sodium sulfate; and solid fragrance (Example 2-spray dried spearmint type; Example 3-spray dded LISTERINE® essential oils). The mixture was mixed until the materials were evenly dispersed, generally in the range from about 3 to 26 minutes with longer mixing times being required for larger batch sizes. The remainder of the PTFE not used in the premix was then added. The mixture was mixed for one additional minute. Detergent was then added to the mixture and the mixture was mixed up to a maximum of 3 additional minutes (the detergent was "LATHONAL", an anionic detergent comprised of 70% sodium lauryl sulfoacetate and 30% sodium chloride). Total maximum mixing time was 30 minutes. The resultant mixture was compressed into a tablet having a diameter of from 3/4" to 15/16", a thickness of 0.16", and a minimum hardness of 12 SCU.

The compositions of the tablets prepared according to Examples 1-3 are set forth in Table 1.

TABLE 1

Tablet Composition

| | Example | | |
|---|---|---|---|
| | 1 | 2 | 3 |
| Sodium Perborate Monohydrate | 387 | 908.0 | 908.0 |
| Sodium Perborate Anhydrous | 83.0 | 365.0 | 365.0 |
| Na$_4$EDTA.2H$_2$O | 119.0 | 540.0 | 540.0 |
| "OXONE" (Potassium Mono Persulfate) | 1221.0 | 552.0 | 552.0 |
| Sodium Saccharin | 7.0 | 7.0 | 7.0 |
| "LATHONOL" | 20.0 | 17.2 | 17.2 |
| PTFE | 3.0 | 19.0 | 19.0 |
| Fragrance Spray Dried Spearmint Type | 30.0 | — | 45.0 |
| Mixed Fragrances Spray Dried (LISTERINE ® Essential Oils) | — | 45.0 | — |
| Color | 5.1 | 5.05 | 5.05 |
| Sodium Tripolyphosphate | 318.0 | 74.3 | 74.3 |
| Na$_2$CO$_3$ | 285.0 | — | — |
| Sodium Sulfate | 150.0 | 67.5 | 67.3 |
| Citric Acid | 119.0 | — | — |
| NaHCO$_3$ | 342.0 | 25.0 | 25.0 |
| Sodium Benzoate | 20.0 | — | — |
| water | 10.0 | — | — |
| Total Weight (grams per 1000 tablets) | 3129.0 | 2625.1 | 2624.9 |

Example 1 is a comparative prior art example of a known composition showing a composition having a higher weight percent of monopersulfate and a lower perborate monohydrate weight percent compared to the inventive compositions. Example 1 also has a low level of EDTA.

Example 2 comprises an example of the invention. Example 2 has a high level of EDTA. Example 2 is the inventive composition with increased spray dried fragrance (LISTERINE® essential oils). Example 2 is a composition having a higher weight percent of perborate monohydrate and a lower weight percent of monopersulfate compared to the known composition of Example 1.

Example 3 is the same as Example 2 except the fragrance is predominantly a spray dried spearmint type which also retains the fragrance when the solution is allowed to stand overnight.

Example 4—Stain and Plaque Removal

Tablets were tested for their cleaning ability on tiles that had been coated with a combination of plaque and various food stains of coffee, tea, blueberry and grape juice.

Sets of plaque-coated and food-stained denture tiles were prepared as follows:

Step I: The denture tiles were immersed in a solution containing human saliva and a growth medium. Plaque was allowed to accumulate over 16 hours at 37° C.

Step II: The tiles were removed from the saliva medium and allowed to air dry for a minimum of two hours.

Step III: The plaque coated tiles were then immersed in a solution of coffee, tea, blueberry, and grape juice for 16 hours at room temperature.

Step IV: Step I, II, and III were repeated two additional times.

Separate sets of plaque-coated and food-stained tiles (5 tiles in each set) were immersed in beakers containing 125 ml of water at 45° C. Tablets of the compositions of Examples 1–3 were added to separate beakers. At the end of 15 minutes, the treated tiles were dunked in a 200 ml volume of tap water 20 times and the rinsing repeated again with 200 ml of tap water. The tiles were allowed to air dry at room temperature. The tiles were then examined for stain removal.

All three samples removed about the same amount of tartar from the denture tiles. These results indicate that the inventive compositions provide cleaning similar to known denture cleansing formulations.

Example 5—Plaque Removal

Sets of plaque-coated denture tiles were prepared as follows:

Step I: The denture tiles were immersed in a solution containing human saliva and a growth medium. Plaque was allowed to accumulate over 16 hours at 37° C.

Step II: The tiles were then removed from the saliva medium and allowed to air dry at room temperature for at least one day.

Separate sets of tiles were immersed in beakers containing 125 ml of water at 45° C. Tablets of the compositions of Examples 1–3 were added to separate beakers. At the end of 15 minutes the treated tiles were rinsed by being dunked in a 200 ml volume of tap water 20 times. The rinsing was repeated again with 200 ml of tap water and the tiles were allowed to air dry at room temperature. The tiles were then stained to highlight the presence of plaque, and were visually inspected.

All three samples removed about the same amount of tartar from the denture tiles. These results indicate that the inventive compositions provide cleaning similar to known denture cleansing formulations.

Example 6—Tartar Removal

Sets of tartar and plaque-coated denture tiles were prepared as follows:

Step I: A set of denture tiles were allowed to rotate through a medium of 70 ml of human saliva containing 0.1% of added Calcium Phosphate, Monobasic, and adjusted to a pH of 7.

Step II: The tiles were rotated through a solution for four 24-hour periods using a fresh calcium/saliva solution for each 24-hour immersion period.

Step III: The tiles were air dried at room temperature prior to use for at least two hours.

These tiles were immersed in separate beakers containing 125 ml of water at 45° C. Tablets of the compositions of Examples 1–3 were added to separate beakers. After 15 minutes, the tiles were dunked in 200 ml of tap water 20 times, and the rinsing was repeated again with another 200 ml of tap water. The tiles were then allowed to air dry at room temperature. The tiles were then subjected to a solution of coffee, tea, blueberry and grape as a disclosant and inspected for the presence of tartar.

All three samples removed about the same amount of tartar from the denture tiles. These results indicate that the inventive compositions provide cleaning similar to known denture cleansing formulations.

Example 7: Effect on the Residual Amount of Active Oxygen on Stained and Non-stained Plaque Tiles It had been observed that the inventive compositions retained about 80% or more of their active oxygen levels while standing for 6 hours. A comparison was performed between the use of tiles having a stained coating on a plaque matrix and tiles which are free of stains and plaque.

(A) The plaque-coated and food-stained denture tiles were prepared as in Example 4.

One set of stained-plaque tiles (3 tiles per set) was immersed in a beaker containing 375 ml of $H_2O$ at 45° C. Tablets of the composition of Example 2 were added to the beaker. At the end of 30 minutes and 6 hours of soaking, 3–10 ml aloquots were assayed for active oxygen content.

(B) A second set of the stain-plaque free tiles (3 tiles per set) was immersed in a beaker containing 375 ml of $H_2O$ at 45° C. Tablets of the composition of Example 2 were added to the beaker. At the end of 30 minutes and 6 hours of soaking, 3–10 ml aloquots were assayed for active oxygen content.

The active oxygen results of this comparison is as follows:

A. Results after 30 minutes 129.0 mg/tablet
130.0 mg/tablet

Active oxygen retained = $\frac{129.5}{*149.0}$ = 86.9%

B. Results after 30 minutes 139.0 mg/tablet
135.0 mg/tablet

Active oxygen retained = $\frac{137.0}{*149.0}$ = 91.94%

A. Results after 6 hours 128.0 mg/tablet
128.0 mg/tablet

Active oxygen retained = $\frac{128.0}{*149.0}$ = 85.9%

B. Results after 6 hours 138.0 mg/tablet
137.0 mg/tablet

Active oxygen retained = $\frac{137.5}{*149.0}$ = 92.3%

*149 represents the 100% active oxygen content of a hypothetical formulation.

These results show that the solutions with the stained-plaque tiles had approximately 86% active oxygen content remaining even after six hours (essentially unchanged from the active oxygen content present at 30 minutes); the solutions with stained-plaque free tiles had approximately 92% active oxygen content remaining even after six hours (essentially unchanged from the active oxygen content present at 30 minutes). These results indicate that the product provides a residual stable reservoir of active oxygen to maintain the denture in a disinfectant during an overnight soak.

Example 8—Fragrance Levels

In order to compare the fragrance levels of the compositions, the tablet of Example 1 was compared to the tablets of Example 2 for dry tablet odor. The physical results are set forth in Table 2 below demonstrate the uniformity of the inventive compositions. The inventive compositions exhibited a pronounced fragrance level in the dry tablet.

Example 1 was compared to Example 2 for solution fragrance evolution by placing one tablet of each example in 120 ml of water at 45° C. and smelling the burst of fragrance. The composition prepared according to the invention exhibited an enhanced burst of fragrance in solution. When the solutions were allowed to stand for one hour at room temperature, the inventive composition exhibited a pronounced fragrance level, whereas the comparative prior art Example 1 exhibited a chlorine like odor. When the solutions were allowed to continue to stand overnight (16 Hours) the inventive composition of Example 2 exhibited an enhanced fragrance retention level, whereas the prior art formulation Example 1 continued to exhibit a chlorine-like odor. This enhanced fragrance level is believed to be due to the lower amounts of hypochlorite in the inventive composition. This feature allows for the use of lower amount of fragrance in the composition and helps to solve problems associated with stability of some fragrances.

TABLE 2

| Fragrance | | | |
|---|---|---|---|
| | Example | | |
| | 1 | 2 | 3 |
| pH | 8.3 | 9.65 | 9.60 |
| Fade Time (Min.) | 12 | 5 | 5 |
| Bomb Value | 4 | 14 | 4 |
| Theoretical Active Oxygen (mg.) | 115 | 170.2 | 170.2 |
| Actual Active Oxygen (mg.) | 114.0 | 165.7 | 165.8 |
| Disintegration Time (seconds) | 180 | 50 | 50 |
| Density (100 Taps) | N/A | N/A | N/A |
| Thickness (inch) | 0.190 | N/A | N/A |
| Diameter (inch) | 57/64 | N/A | N/A |

Example 9—Granulation Formulations

A denture cleaning composition was prepared as a dispersible powder as follows. The amounts of each ingredient in the composition are set forth in Table 3.

Example 9 was prepared as follows: A pregranulation mix, or premix, was prepared containing anhydrous sodium perborate, sodium perborate monohydrate, and PTFE (#1, 2, and 3). These three components were blended in a suitable blender for about 3 minutes and passed through a chilsonating compacting machine, Model DMC Fitzpatrick, under the following conditions: The chilsonator was set at an air pressure of from about 88 to about 90 psi, and oil pressure of from about 2300 to about 2400 psi, and the roller at high speed using 2–3 amps. The compacted material was then passed through a model 197S comil having an 0.175 inch spacer, with an 0.032 inch screen at 4200 RPM. The compacted anhydrous perborate, perborate monohydrate and PTFE in the premix had a U.S.S. Mesh distribution of:

0% on a size 20 mesh screen, 14.2% on a size 40 mesh screen, 26.4% on a size 60 mesh screen, 14.8% on a size 80 mesh screen, 11.1% on a size 100 mesh screen, 33.5% through a 100 mesh screen.

The premix had an untopped density of 0.593 grams/ml and a tapped density (100 taps) of 0.853 grams/ml.

In a suitable blender container set at 50 RPM, a preblend of the following ingredients was preformed for 3 minutes: 8, 9, 10, 11, 13, and 15.

The material specifications for certain ingredients in each of the invention compositions are as follows:

The preferred chelating value of the EDTA is greater than 248.

The preferred mesh size of the EDTA is as follows:

0.2% Maximum remains on a U.S.S. 20 mesh sieve

25% Maximum remains on a U.S.S. 40 mesh sieve

20% Maximum passes through a U.S.S. 100 mesh sieve

The preferred water content of Sodium Perborate Monohydrate is less than 0.6%.

In a separate preparation, #7 was passed through a 20 mesh screen.

Thereafter, in a one cubic foot ribbon blender set at no higher than 40 RPM, the following ingredients were combined in sequence in evenly spaced intervals: #4, 5, 6, 12, 14, and Pre-blend A. The mixture was blended for about 1–1-½ minutes. #7 was then added and the mixture was blended for an additional minute. Approximately 2.018 grams of the resulting granulation was packaged in a 0.0007" aluminum composite foil pouch and hermetically sealed from moisture and light.

TABLE 3

| INGREDIENT | PERCENT W/W | INGRED. QUANTITY PER 2017.789 |
|---|---|---|
| PREMIX A | | |
| 1. Sodium Perborate Monohydrate | 45.2600 | 242.2619 MGS |
| 2. Sodium Perborate Anhydrous | 54.1800 | 290.0077 MGS |
| 3. Polytetrafluoroethylene | .5600 | 2.9975 MGS |
| TOTALS | 100.0000 | 535.2670 MGS |
| BLUE GRANULATION | 23.6982 | 478.1800 MGS |
| 4. Sodium Perborate Monohydrate | 21.2222 | 428.2200 MGS |
| 5. EDTA WL250 Partially Hydrated | 21.6940 | 437.7400 MGS |
| 6. Potassium Monopersulfate | .8708 | 17.5700 MGS |
| 7. LATHANOL | .0981 | 1.9800 MGS |
| 8. FD & C Yellow No. 5 Aluminum Lake, (15–17%) | 2.9200 | 58.9200 MGS |
| 9. Sodium Tripolyphosphate Anhydrous Granular | .3543 | 7.1500 MGS |
| 10. Sodium Saccharin USP Powder | .0352 | .7100 MGS |
| 12. FD & C Red No. 40 Al Lake | 2.2778 | 45.9600 MGS |
| 13. Flavor Blend Special N & A, 841082 | .2314 | 4.6690 MGS |
| 14. FD & C Blue No. 2 - 87% | 26.5276 | 535.2700 MGS |
| 15. Premix A | .0704 | 1.4200 MGS |
| 16. FD & C Blue No. 2 Lake (Lakolene B301) | | |
| TOTALS | 100.0000 | 2017.7890 MGS |

The granulation has an active oxygen content of 130.0 mg/tablet; a pH of 9.6 (9.30 9.90) after 5 minutes in 120 ml of $H_2O$ at 45° C.; fade of blue to light yellow; fade time of blue fading to yellow within 3 minutes in 120 ml of $H_2O$ at 45° C.; a maximum disintegration time of 180 seconds in 120 ml of $H_2O$ at 45° C. and maximum bomb test of 30 psig in 120 ml of $H_2O$ at 85° C. for 1 hour.

The purpose of the above Examples is to illustrate some embodiments of the present invention without implying limitations. It will be apparent to those skilled in the art that various modifications and variations may be made in the apparatus or procedure of the invention without departing from the scope or spirit of the invention.

We claim:

1. A denture cleansing composition derived from a mixture comprising:

(a) a pregranulated compressed mixture of an anhydrous perborate in an amount of from about 5% to about 25% by weight of said composition, a perborate monohydrate, and a lubricant and compression aid, wherein the weight ratio of anhydrous perborate to said perborate monohydrate in said pregranulated mixture is from about 1:3 to about 1:1, the amount of perborate monohydrate in the premixture being reflected by the ratio; and (b) a monopersulfate compound in an amount of from about 15% to about 27% by weight of said composition; and (c) non-granulated perborate monohydrate wherein the total amount of granulated and non-granulated perborate monohydrate is in an amount of from about 30% to about 60% by weight of said denture cleansing composition; and (d) an effective amount of a sequestering agent to remove calcium deposits and calculus deposits.

2. The denture cleansing composition of claim 1 wherein;

(i) said anhydrous perborate is potassium or sodium anhydrous perborate;

(ii) said lubricant and compression aid is in an amount of from about 0.1% to about 0.8% by weight of said pregranulated compressed mixture, and wherein said lubricant and compression aid is polytetrafluorethylene;

(iii) said monopersulfate compound is a triple potassium salt with the formula $KHSO_5 \cdot KHSO_4 \cdot K_2SO_4$ and a mole ratio of 2:1:1; and (iv) said sequestering agent is in an amount of from about 1% to about 25% by weight of said composition, and wherein said sequestering agent is $Na_4EDTA \cdot 2H_2O$.

3. The composition of claim 1, wherein said anhydrous perborate comprises from about 10% to about 20% by weight of said composition.

4. The composition of claim 1, wherein said anhydrous perborate comprises from about 13% to about 14% by weight of said composition.

5. The composition of claim 1, wherein said perborate monohydrate comprises from about 30% to about 40% by weight of the total cleansing composition.

6. The composition of claim 1, wherein said perborate monohydrate comprises from about 33% to about 35% by weight of the total cleansing composition.

7. The composition of claim 1 wherein said lubricant and compression aid is polytetrafluourethylene.

8. The composition of claim 1, wherein said lubricant and compression aid comprises from about 0.1% to about 0.8% by weight of the pregranulated compressed mixture.

9. The composition of claim 1 wherein said monopersulfate compound is a triple potassium salt with the formula $KHSO_5 \cdot KHSO_4 \cdot K_2SO_4$ and a mole ratio of 2:1:1.

10. The composition of claim 9, wherein said monopersulfate compound comprises from about 15% to about 27% by weight of said composition.

11. The composition of claim 1, wherein said sequestering agent is EDTA.

12. The composition of claim 11, wherein said EDTA is Na₄EDTA·2H₂O.

13. The composition of claim 12, wherein said Na₄EDTA·2H₂O comprises from about 1% to about 25% by weight of said composition.

14. The composition of claim 13, wherein the mesh-size profile of said EDTA is a maximum of 40% through U.S.S. 100 mesh sieve, a maximum of 65% on the U.S.S. 40 mesh sieve and a maximum of 0.2% remaining on the U.S.S. 20 mesh sieve.

15. The composition of claim 13, wherein the mesh-size profile of the said EDTA is in the range of a maximum of 20% through U.S.S. 100 mesh sieve, a maximum of 25% on the U.S.S. 40 mesh sieve and a maximum of 0.2% remaining on the U.S.S. 20 mesh sieve.

16. The composition of claim 12, wherein the chelating value of said Na₄EDTA·2H₂O is at least about 248.

17. The composition of claim 1, wherein said monopersulfate is selected from the group consisting of alkali metal monopersulfates and alkaline earth metal monopersulfates.

18. The composition of claim 1, wherein said monopersulfate is sodium or potassium monopersulfate.

19. The composition of claim 1, wherein said anhydrous perborate is selected from the group consisting of alkali metal perborates and alkaline earth metal perborates.

20. The composition of claim 1, wherein said anhydrous perborate is potassium or sodium anhydrous perborate.

21. The composition of claim 1, wherein the weight ratio of perborate monohydrate to anhydrous perborate to polymeric fluorocarbon compound is about 54.2:45.2:0.6.

22. The composition of claim 1, wherein said perborate monohydrate is potassium or sodium perborate monohydrate.

23. The composition of claim 1, wherein the weight ratio of perborate monohydrate/monopersulfate compound is from about 3:1 to about 1:1.

24. The composition of claim 23, wherein the weight ratio of perborate monohydrate/monopersulfate compound is about 1.7:1.

25. The composition of claim 1, wherein the free surface water moisture content of a tablet made from said composition comprises preferably less than about 0.3% by weight of the composition.

26. The composition of claim 1, wherein a detergent is a component of said composition.

27. The composition of claim 26, wherein said detergent is an anionic detergent.

28. The composition of claim 27, wherein said anionic detergent is present in the amount of up to about 5% by weight of the composition.

29. The composition of claim 1, wherein the tablet composition is characterized by active oxygen levels in the range from about 100 to about 200 mg/tablet.

30. The composition of claim 1, wherein the composition is characterized by fragrance retention levels greater than about 50% throughout a period of six hours or greater.

31. The composition of claim 1, wherein the composition is characterized by fragrance retention levels greater than about 50% throughout a period of 16 hours.

32. A process for preparing a denture cleansing composition according to claim 1 comprising the steps of:
(a) preparing a compacted compressed mixture comprising anhydrous perborate salts and perborate monohydrate salts in combination with a lubricant and compression aid; and
(b) grinding said compacted mixture into a pregranulation mixture, or premix; and
(c) adding the pregranulation mixture, or premix, to the other materials in the denture cleansing composition and mixing; and
(d) adding detergent to the mixture and mixing for up to 3 minutes; and
(e) forming the resultant blended mixture into a cohesive tablet.

33. The process of claim 32 wherein said compacted mixture is pre-dried to a free moisture level of about 0.3% to about 1.5% by weight of the compacted mixture.

34. The process of claim 33 wherein said compacted mixture is pre-dried to a free moisture level of less than about 0.3% by weight of the compacted mixture.

35. A denture cleansing composition derived from a mixture comprising:
(a) a pregranulated compressed mixture of an anhydrous perborate in an amount of from about 5% to about 25% by weight of said composition, a perborate monohydrate, and a lubricant and compression aid, wherein the weight ratio of anhydrous perborate to said perborate monohydrate in said pregranulated mixture is from about 1:3 to about 1:1, the amount of perborate monohydrate in the premixture being reflected by the ratio;
(b) a monopersulfate compound in an amount of from about 15% to about 27% by weight of said composition;
(c) non-granulated perborate monohydrate wherein the total amount of granulated and non-granulated perborate monohydrate is in an amount of from about 30% to about 60% by weight of said denture cleansing composition;
(d) an effective amount of a sequestering agent to remove calcium deposits and calculus deposits; and
(e) an effective amount of at least one fragrance.

36. The composition of claim 35 wherein the fragrance is thymol.

37. The composition of claim 35 wherein the fragrance is eucalyptol.

38. The composition of claim 35 wherein the fragrance is methyl salicylate.

39. The composition of claim 35 wherein the fragrance is menthol.

40. A process for preparing a denture cleansing composition according to claim 35 comprising the steps of:
(a) preparing a compacted compressed mixture comprising anhydrous perborate salts and perborate monohydrate salts in combination with a lubricant and compression aid;
(b) grinding said compacted mixture into a pregranulation mixture, or premix;
(c) adding the pregranulation mixture, or premix, to the other materials in the denture cleaning composition and mixing;
(d) adding detergent to the mixture and mixing;
(e) adding at least one fragrance to the mixture; and
(f) forming the resultant blended mixture into a cohesive tablet.

41. The process for claim 41 wherein the fragrance is selected from the group consisting of thymol, eucalyoptol, methyl salicylate and menthol.

* * * * *